US00PP35699P2

(12) United States Plant Patent
Dirr

(10) Patent No.: US PP35,699 P2
(45) Date of Patent: Mar. 19, 2024

(54) ***DISTYLIUM* PLANT NAMED 'DISMD-15-18'**

(50) Latin Name: ***Distylium* sp. hybrid**
Varietal Denomination: DISmd-15-18

(71) Applicant: University of Georgia Research Foundation, Inc., Athens, GA (US)

(72) Inventor: Matthew A. Dirr, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 18/142,706

(22) Filed: May 3, 2023

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP24,410 P3 * 4/2014 Dirr ..... A01H 5/02
Plt./226

* cited by examiner

*Primary Examiner* — Karen M Redden
(74) *Attorney, Agent, or Firm* — Thomas | Horstemeyer, LLP

(57) ABSTRACT

A new and distinct cultivar of *Distylium* plant named 'DISmd-15-18', characterized by its compact, mounding and evergreen growth habit, and its ovate-elliptical shaped leaves, that are dark green once mature and blueish-purple in color when young. The inventor believes it could be used as a foundation plant in the southern United States.

2 Drawing Sheets

Botanical designation: *Distylium* sp. hybrid.
Cultivar denomination: 'DISmd-15-18'.

BACKGROUND OF THE INVENTION

The present invention relates to a new and distinct cultivar of *Distylium* plant, botanically known as *Distylium* sp. hybrid (*Distylium myricoides* x *Distylium racemosum*), a member of the Hamamelidaceae, and hereinafter referred to by the cultivar name 'DISmd-15-18'. This cultivar represents a new *Distylium*, an evergreen shrub grown for landscape use.

The new cultivar was discovered and selected from a breeding program conducted by the inventor at a horticulture farm in Watkinsville, GA in 2018. 'DISmd-15-18' originated as a seedling that arose from a group of seedlings from the open pollination of the female parent *Distylium* 'PIIDIST-II' (U.S. Plant Pat. No. 24,409, also called Blue Cascade™) 'DISmd-15-18' was selected as a single unique plant in the summer of 2018 from among the resulting seedlings.

Asexual propagation of the new cultivar by stem cutting was first performed by the inventor in Watkinsville, Ga in 2018 and has continued since then. Observations of the resulting asexually propagated 'DISmd-15-18' progeny have shown that the unique characteristics of the new cultivar are stable and reproduced true-to-type in successive generations.

SUMMARY OF THE INVENTION

Plants of the new *Distylium* cultivar 'DISmd-15-18' have not been observed under all possible environmental conditions. The phenotype may vary somewhat with variations in environment and cultural practices such as temperature, water and fertility levels, soil types, and light intensity without, however, any variance in genotype.

The following traits have been repeatedly observed and represent the unique and distinguishing characteristics of the new *Distylium* cultivar named 'DISmd-15-18'. In combination, these traits set 'DISmd-15-18' apart from all other existing varieties of *Distylium* known to the inventors:

1. 'DISmd-15-18' exhibits a compact, mounding, cascading growth habit.
2. 'DISmd-15-18' exhibits leaves that are dark green when mature and blueish-purple when immature or juvenile.
3. 'DISmd-15-18' exhibits maroon-red flowers.
4. 'DISmd-15-18' has thus far exhibited cold hardiness to about 20 degrees Fahrenheit in trials.

Plants of 'DISmd-15-18' differ from its female parent and closest commercial cultivar, 'PIIDIST-II' at least in growth habit, foliage color, and cold hardiness. Plants of 'DISmd-15-18' have a smaller, more compact, mounded, cascading growth habit; smaller, lustrous dark blue-green mature foliage; and increased cold hardiness, whereas plants of 'PIIDIST-II' have a larger, less compact, upright, spreading growth habit; larger medium green foliage; and are less cold hardy.

BRIEF DESCRIPTION OF THE DRAWINGS

The accompanying color photographs illustrate the overall appearance and distinct characteristics of the new cultivar of *Distylium* 'DISmd-15-18', showing the colors as true as it is reasonably possible to obtain in color reproductions of this type. Colors in the photographs may differ slightly from the color values cited in the detailed botanical description, which accurately describes the colors of the new *Distylium* 'DISmd-15-18'.

The photograph labeled

The photograph labeled

DETAILED DESCRIPTION

Figure 1:
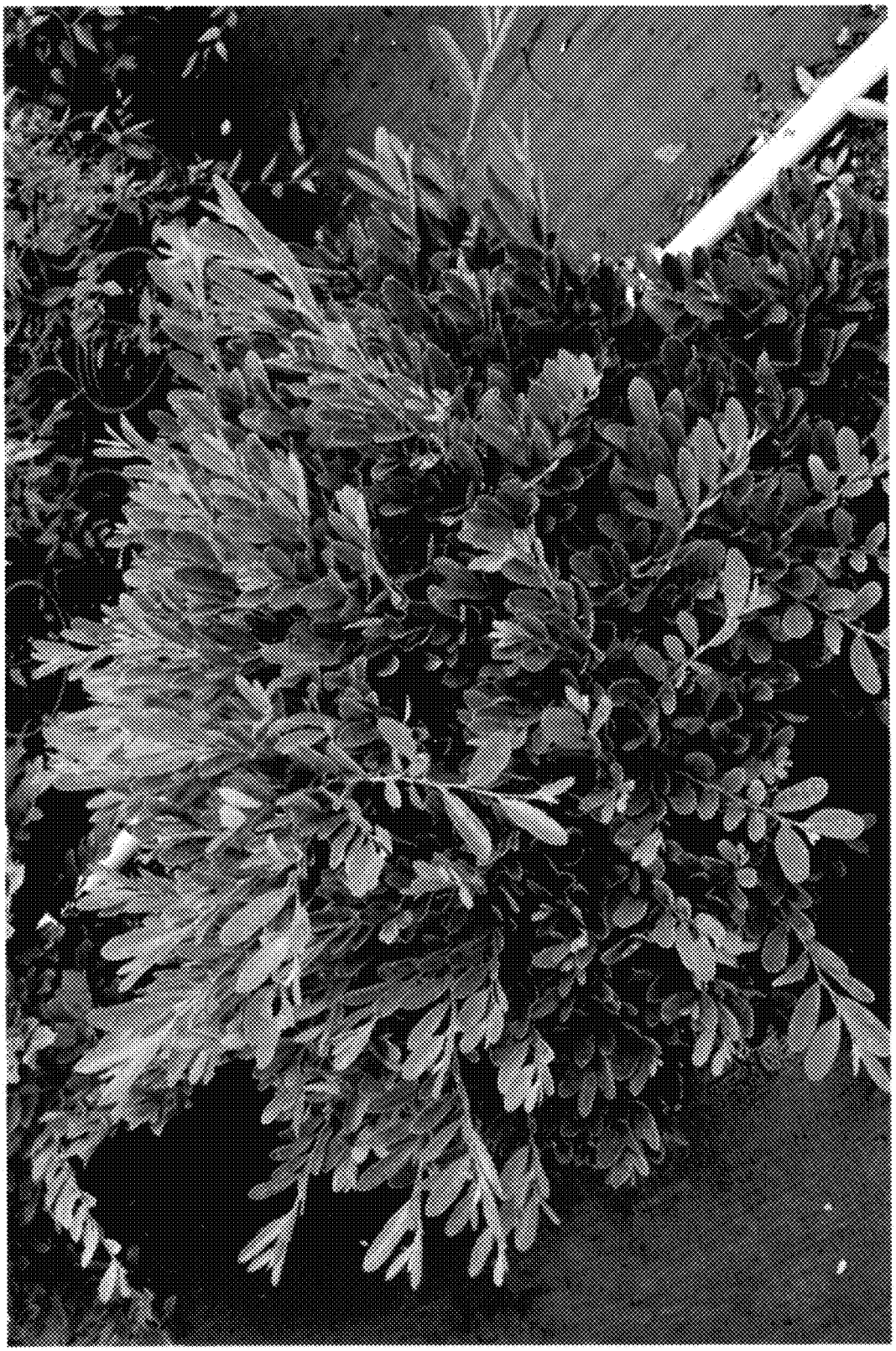
FIG. 1 depicts a 'DISmd-15-18' plant with no damage grown at the horticultural farm in Watkinsville, GA. Plants are 2 years old, and the photo was taken in May 2019.
Figure 2:
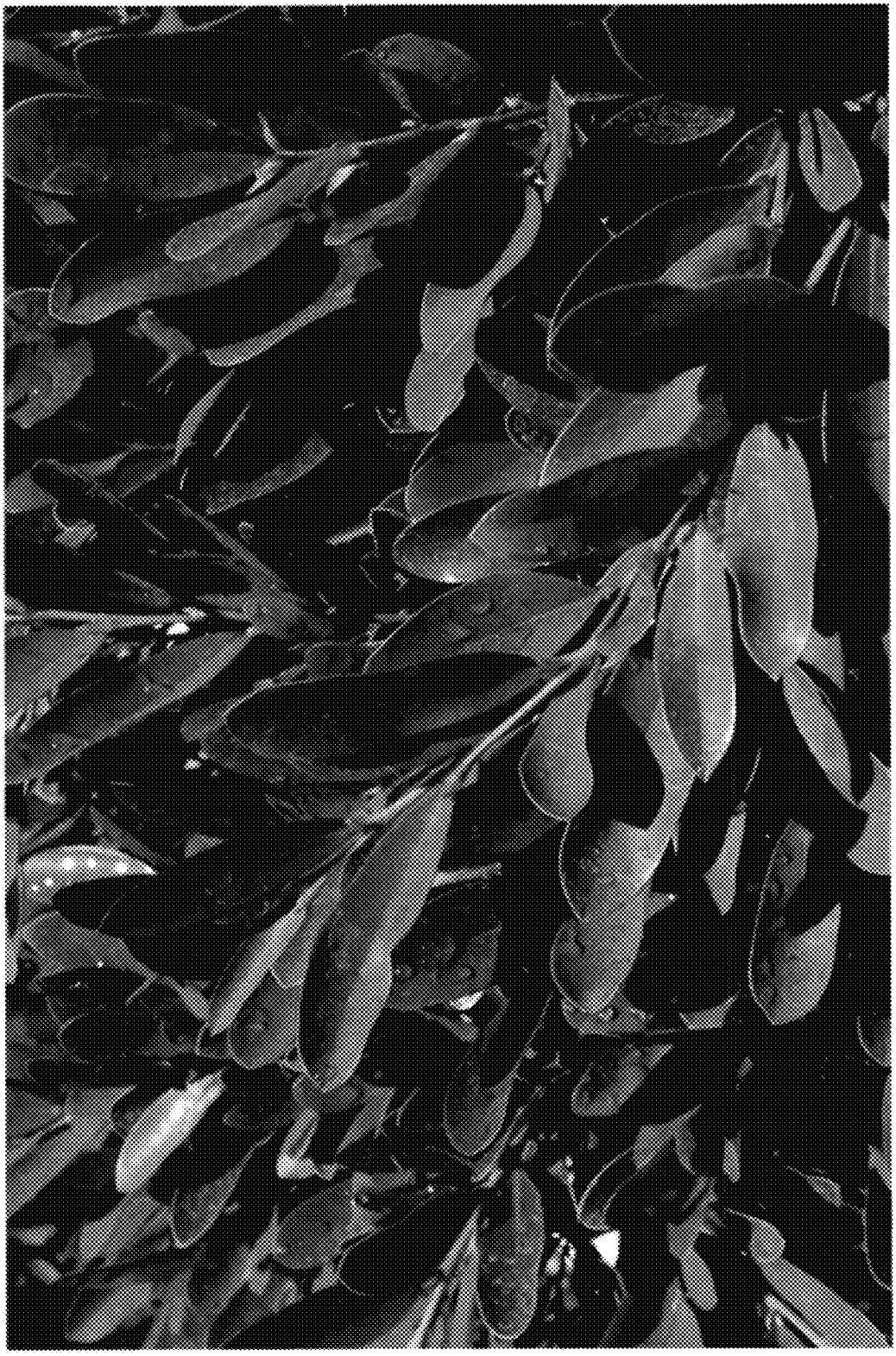
FIG. 2 depicts a close-up view of 'DISmd-15-18' showing the dark green leaves and blueish-purple new foliage. Plants are 2 years old, and the photo was taken in May 2019.

The following traits have been consistently observed in the original plant of this new variety and in asexually propagated progeny grown in Watkinsville, Georgia, and, to the best knowledge of the inventors, their combination forms the unique characteristics of the new variety of *Distylium* 'DISmd-15-18'.

Throughout this specification, color names beginning with a small letter signify that the name of that color, as used in common speech, is aptly descriptive. Color names beginning with a capital letter designate values based upon The Royal Horticultural Society Colour Wheel, 2015 Edition, published by The Royal Horticultural Society, London, except when general terms of ordinary dictionary significance are used.

The aforementioned photographs and following observations, measurements, and values describe plants of the *Distylium* cultivar named 'DISmd-15-18'. Data were collected from plants that were approximately 3 years old and were grown in three-gallon containers under outdoor conditions in Watkinsville, GA. The average low temperatures ranged from lows of about 33° F. to 42° F. in the winter, to average high temperatures of about 85° F. to 92° F. in summer.

Botanical classification: *Distylium* sp. hybrid, cultivar 'DISmd-15-18'.

Commercial classification: Ornamental shrub plant.

Parentage: *Distylium* sp. hybrid. (Female or seed parent: 'Blue Cascade' *Distylium*; Male or pollen parent: unknown/open pollenated).

Propagation: Stem cuttings, asexual propagation.

Time to initiate roots in summer: About 3 to 4 weeks at 32° C.

Time to produce a rooted young plant: About 4 months at 32° C.

Plant description: Broadleaf evergreen flowering shrub; multi-stemmed; compact, mounded, cascading growth habit. Freely branching; removal of the terminal bud enhances lateral branch development.

- *Usage*.—Landscaping hedge appropriate for commercial use, home garden, and the like.
- *Root description*.—Medium, well branched.
- *Plant size*.—The original plant, now about 2 years old in the ground, is about 30 cm high from the soil level to the top of the foliage canopy and about 64 cm wide.
- *First year stems*.—Having a diameter of about 2 mm. Shape: Round. Fine pubescence. Few small lenticels about 1 mm in diameter and N199B in color. Length: 20 cm and very flexible.
- *First year stem color*.—146B.
- *Second year and older stems*.—Have a diameter of about 4 mm or more. Shape: Round. Length: 16 cm and smooth with no pubescence.
- *Second year and older stem color*.—199A.
- *Stem strength*.—Flexible when young, less flexible when mature.
- *Internode length*.—About 2 cm.
- *Trunk diameter*.—About 2 cm at soil level.
- *Color*.—199A.
- *Bark*.—Does not exfoliate, covered with many lenticels about 2 mm in diameter and N199B in color.

Vegetative bud description:

- *Arrangement*.—Alternate, simple.
- *Shape*.—Ovoid with fused, pubescent bud scales.
- *Size*.—About 2.5 mm in length and about 2 mm in width.
- *Color*.—N199A.

Foliage description:

- *Arrangement*.—Alternate, simple.
- *Length*.—About 4 cm.
- *Width*.—About 2 cm.
- *Shape*.—Ovate-elliptical.
- *Apex*.—Acute.
- *Base*.—Cuneate.
- *Margin*.—Usually entire, but occasionally with few broad serrations at apex.
- *Texture* (*upper and lower surfaces*).—Thick, leathery.
- *Venation pattern*.—Pinnate.
- *Venation color* (*upper and lower surfaces*).—Midrib color is 145C and secondary vein color is 147A.
- *Color of emerging foliage* (*upper surface*).—N144C.
- *Color of emerging foliage* (*lower surface*).—144C.
- *Color of mature foliage* (*upper surface*).—147A.
- *Color of mature foliage* (*lower surface*).—146B.
- *Petiole length*.—About 4 mm.
- *Petiole diameter*.—About 1 mm.
- *Fine pubescence*.—199B in color.
- *Petiole color* (*upper and lower surfaces*).—144B.

Flower description:

- *Flower type and habit*.—Apetalous flowers with a pubescent, 5-parted calyx are borne on short racemes from the leaf axils.
- *Natural flowering season*.—Late winter, approximately January to February in Watkinsville, Ga. Individual flowers are showy for approximately 1 week and are self-cleaning. The inflorescence is a raceme about 2.5 cm in length and 1.4 cm in width, consisting of 4 to 10 flowers per raceme that are 1876 in color. A lateral branch may have 15 to 20 inflorescences.
- *Flower size*.—About 6-8 mm in diameter and about 8 mm in height.
- *Pedicels*.—About 2 mm in length.
- *Peduncles*.—About 1 cm in length.
- *Color*.—Pedicels and peduncles 146B in color with pubescence 166A in color.

Stamens description:

- *Quantity/arrangement*.—8 to 10 per flower.
- *Filament*.—About 2.5 mm in length, less than about 1 mm in width, and 146D in color.
- *Anthers*.—About 2 mm in length, about 1 mm in width, and 59A in color.
- *Pollen*.—Produced in moderate quantities and is 158D in color.

Pistils description:

*Position*.—Superior.

*Size*.—About 6 mm in length and about 2.5 mm in width.

*Color*.—146D.

*Stigma*.—2 per pistil, about 4 mm in length, 185B in color.

*Style*.—2 per flower, about 2 mm in length, and 146D in color.

*Ovary*.—Two per flower, about 2 mm in diameter, about 2 mm in height, and 146D in color.

Fruit description:

*Type/appearance*.—2-valved, beaked woody capsule containing 2 seeds, one per valve.

*Fruit size*.—The capsule is about 1.5 cm long and about 7 mm wide.

*Mature color*.—200C.

*Seeds*.—Oblong to elliptical in shape, about 6 mm in length, about 3 mm in width, and N200A in color.

Disease/pest resistance: Plants of the new *Distylium* grown in the nursery and garden have not been noted to be susceptible to pathogens, pests, or disease.

Weather and temperature tolerance: 'DISmd-15-18' is cold hardy in USDA Cold Hardiness Zones 6-9.

It is claimed:

1. A new and distinct cultivar of *Distylium* plant named 'DISmd-15-18' as illustrated and described herein.

* * * * *